United States Patent [19]

Zilch et al.

[11] Patent Number: 5,563,257

[45] Date of Patent: Oct. 8, 1996

[54] PHOSPHOLIPID DERIVATIVES OF NUCLEOSIDES

[75] Inventors: Harald Zilch, Mannheim; Herbert Leinert, Heppenheim; Alfred Mertens, Schriesheim; Dieter Herrmann, Heidelberg, all of Germany

[73] Assignee: Boehringer Mannheim GmbH, Mannheim, Germany

[21] Appl. No.: 438,240

[22] Filed: May 9, 1995

Related U.S. Application Data

[63] Continuation of Ser. No. 969,252, Sep. 7, 1993, abandoned.

[30] Foreign Application Priority Data

Aug. 20, 1990 [DE] Germany ............ 40 26 265.0

[51] Int. Cl.⁶ .................... C07H 19/10; C07H 19/20
[52] U.S. Cl. ........................ 536/26.14; 536/26.1
[58] Field of Search ............... 536/26.14, 26.1

[56] References Cited

U.S. PATENT DOCUMENTS

| | | | |
|---|---|---|---|
| 4,283,394 | 8/1981 | West et al. | 424/180 |
| 4,291,024 | 9/1981 | Turcotte | 424/180 |
| 4,622,392 | 11/1986 | Hona et al. | 536/26.2 |
| 4,921,951 | 5/1990 | Shuto et al. | 536/26.1 |
| 5,194,654 | 3/1993 | Hostetler et al. | 558/152 |
| 5,223,263 | 6/1993 | Hostetler et al. | 424/450 |

FOREIGN PATENT DOCUMENTS

| | | |
|---|---|---|
| 0262876 | 4/1988 | European Pat. Off. |
| 0350287 | 1/1990 | European Pat. Off. |
| 0376518 | 7/1990 | European Pat. Off. |
| 0457570 | 11/1991 | European Pat. Off. |
| 290197 | 11/1989 | Germany |
| 4111730 | 4/1991 | Germany |
| 9008769 | 8/1990 | WIPO |
| 9217487 | 4/1991 | WIPO |

OTHER PUBLICATIONS

Hostetler, K. Y., et al., Jour. of Bio. Chem. vol. 265, No. 11, pp. 6112–6117 (1990).
Shuto, S. et al., Tetrahedron Letters, vol. 28, No. 2, pp. 199–202 (1987).
Hong, C. II, et al., J. Med. Chem. vol. 33, pp. 1380–1386 (1990).
Shuto, S., et al., Chem. Pharm. Bull. vol. 36. No. 1, pp. 209–217 (1988).
Shuto, S., et al., Chem. Pharm. Bull. vol. 36, No. 12, pp. 5020–5023 (1988).
Piantadosi, C., et al. J. Med. Chem., vol. 34, pp. 1408–1414 (1991).
Hostetler, K. Y., et al. Journal of Biol. Chem. vol. 266, No. 18, pp. 11714–11717 (1991).
Steim, J. M., et al., Biochem. Biophys. Res. Com., vol. 171, No. 1, pp. 451–457 (1990).
Hong, C. I., et al., Cancer Research vol. 50, pp. 4401–4406 (1990).
Hong, C. I., et al. Lipids, vol. 26, No. 12, pp. 1437–1444 (1991).
Hong, C. I., et al. Drugs of the Future vol. 15, No. 3, pp. 245–253 (1990).
Ryu, E. K., et al. Jour. of Medicinal Chem. vol. 25, No. 11 pp. 1322–1329 (1982).
Lindh, I., et al. Nucleic Acids Res. Symposium Series No. 18 pp. 189–193 (1987).
Meier, C., et al., Bioorganic & Medicinal Chem. Ltrs. vol. 1, No. 10, pp. 527–530 (1991).
Chemical Abstract, Issue 209, 109:93508d, p. 11 (1988).

Primary Examiner—Gary L. Kunz
Attorney, Agent, or Firm—Felfe & Lynch

[57] ABSTRACT

Liponucleotides containing an ether linkage in the 2-position and a thioether, sulfoxide, or sulfone linkage in the 3-position. The nucleoside component of said liponucleotide is AZT or 3'-deoxy-3'-fluorothymidine. These compounds exhibit antiviral activity.

18 Claims, No Drawings

PHOSPHOLIPID DERIVATIVES OF NUCLEOSIDES

This is a Continuation Application of application Ser. No. 07/969,252, filed Sep. 7, 1993, now abandoned.

The subject of the present invention are new phospholipid derivatives of nucleosides of the general formula I,

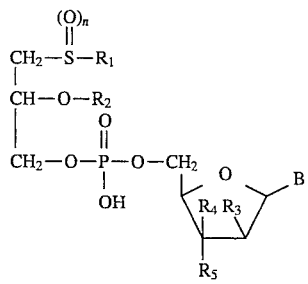

in which $R_1$ signifies a straight-chained or branched, saturated or unsaturated alkyl chain with 8–15 carbon atoms which can possibly be substituted one or more times by phenyl, halogen, $C_1$–$C_6$-alkoxy, $C_1$–$C_6$-alkylmercapto, $C_1$–$C_6$-alkoxycarbonyl, $C_1$–$C_6$-alkylsulphinyl or $C_1$–$C_6$-alkylsulphonyl groups, $R_2$ is a straight-chained or branched, saturated or unsaturated alkyl chain with 8–15 carbon atoms which can possibly be substituted one or more times by phenyl, halogen, $C_1$–$C_6$-alkoxy, $C_1$–$C_6$-alkylmercapto, $C_1$–$C_6$-alkoxycarbonyl or $C_1$–$C_6$-alkylsulphonyl groups, $R_3$ hydrogen or a hydroxyl group, $R_4$, $R_5$ in each case signify hydrogen or one of the radicals $R_4$ and $R_5$ halogen, a hydroxyl, a cyano or an azido group and, furthermore, $R_3$ and $R_4$ can represent a further bond between C-2' and C-3', n is 0, 1 or 2 and B is one of the following compounds:

1.)

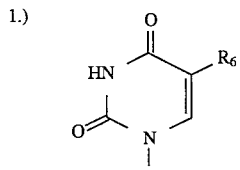

whereby $R_6$ can be hydrogen, an alkyl chain with 1–4 carbon atoms or halogen,

2.)

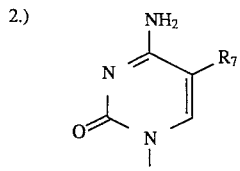

whereby $R_7$ can be hydrogen, an alkyl chain with 1–4 carbon atoms or halogen,

3.)

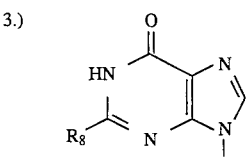

whereby $R_8$ can be hydrogen, an alkyl chain with 1–4 carbon atoms, halogen or a hydroxyl or an amino group,

4.)

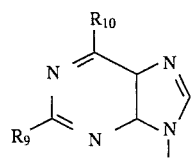

whereby $R_9$ can be hydrogen or an amino group and $R_{10}$ signifies hydrogen, halogen, $C_1$–$C_6$-alkoxy, $C_1$–$C_6$-alkylmercapto or an amino group. The amino group can be mono- or di-substituted by $C_1$–$C_6$-alkyl, $C_1$–$C_6$-alkoxy, hydroxy-$C_2$–$C_6$-alkyl and/or $C_3$–$C_6$-cycloalkyl, aryl, hetaryl, aralkyl or hetarylalkyl groups. The hetarylalkyl groups can possibly be substituted in the aryl or hetaryl radical by one or more hydroxyl, methoxy or alkyl groups or halogen, or allyl which can possibly be substituted with mono- or dialkyl or alkoxy groups, their tautomers and their physiologically acceptable salts of inorganic and organic acids and bases, as well as processes for their preparation and medicaments containing these compounds.

Since the compounds of general formula I contain asymmetrical carbon atoms, all optically-active forms and racemic mixtures of these compounds are also the subject of the present invention.

In J. Biol. Chem. 265, 6116 (1990) is described the preparation and use of liponucleotides as anti-viral medicaments. However, there were here investigated and synthesised only the known nucleosides, such as e.g. AZT and ddC, coupled to dimyristoylphosphatidyl and dipalmitoylphosphatidyl radicals with their fatty acid ester structure.

In J. Med. Chem. 33, 1380 (1990) are described nucleoside conjugates of thioether lipids with cytidine diphosphate which display an antitumour action and could find use in oncology.

In Chem. Pharm. Bull. 36, 209 (1988) are described 5'-(3-SN-phosphatidyl)-nucleosides with anti-leukemic activity, as well as their enzymatic synthesis from the corresponding nucleosides and phosphocholines in the presence of phospholipase D with transferase activity.

The enzymatic synthesis of liponucleotides is, inter alia, also described in Tetrahedron Lett. 28, 199 (1987) and Chem. Pharm. Bull. 36, 5020 (1988).

The compounds of the present invention also display valuable pharmacological properties. In particular, they are suitable for the therapy and prophylaxis of infections which are caused by DNA viruses, such as e.g. herpes simplex virus, the cytomegalovirus, Papovavirus, the varicells zoster virus or Epstein-Barr virus, or RNA viruses, such as togagviruses, or especially retroviruses, such as the oncoviruses HTLV-I and II, as well as the lentiviruses visna and human immune deficiency virus HIV-1 and 2.

The compounds of the formula I appear to be especially suitable for the treatment of the clinical manifestations of the retroviral HIV infection in humans, such as persistent generalised lymphadenopathy (PGL), the advanced state of AIDS-related complex (ARC) and the clinically complete picture of AIDS.

Surprisingly, it has now been found that compounds of the general formula I inhibit the multiplication of DNA and RNA viruses at the stage of the virus-specific DNA and RNA transcription. The substances can influence the multiplication of retroviruses via the inhibition of the enzyme reverse transcriptase (cf. Proc. Natl. Acad. Sci. USA 83, 1911, 1986 or Nature 325, 773, 1987). Of especial therapeutic interest is the inhibiting action on the HIV virus, the cause of the immune deficiency disease AIDS. At present, for the treatment of AIDS, 3'-azido-3'-deoxythymidine (DE-A-3608606) is permitted in the case of AIDS patients. However, some toxic side effects of 3'-azido-3'-desoxythymidine on the bone marrow make blood transfusions necessary in the case of about 50% of the treated patients. The compounds of the general formula I do not posses these disadvantages. They act anti-virally without being cytotoxic in pharmacologically relevant doses.

The compounds of the present invention and their pharmaceutical preparations can also be used, in combination with other medicaments, for the treatment and prophylaxis of the above-mentioned infections. Examples of these further medicaments, which are usable for the treatment and prophylaxis of HIV infections or of diseases accompanying this disease are 3'-azido-3'-deoxythymidine, 2',3'-dideoxynucleosides, such as e.g. 2',3'-dideoxycytidine, 2',3'-dideoxyadenosine and 2',3'-dideoxyinosine, acyclic nucleosides (e.g. acyclovir), interferons, such as A-interferon; renal excretion inhibitors, as as probenicid; nucleoside transport inhibitors, such as dipyridanol; as well as immune modulators, such as interleukin 2, or stimulation factors, such as granulocyte macrophage colony factor. The compounds of the present invention and the other medicaments can, in each case, be administered individually, simultaneously, possibly in a single or two separate formulations or at different times so that a synergistic effect is achieved.

Possible salts of the compounds of the general formula I, include alkali metal, alkalin earth metal and ammonium salts of the phosphate group. As alkali metal salts, lithium, sodium and potassium salts are preferred. As alkaline earth metal salts, magnesium and calcium salts. By ammonium salts, in accordance with the invention, are understood those compounds which contain the ammonium ion which can be substituted up to four times by alkyl radicals with 1–4 carbon atoms and/or aralkyl radicals, preferably benzyl radicals. The substituents on the ammonium ion can be the same or different.

The compounds of the general formula I can contain basic groups, especially amino groups, which can be converted with suitable acids into acid-addition salts. Acids useful for this purpose include, hydrochloric acid, hydrobromic acid, sulphuric acid, phosphoric acid, fumaric acid, succinic acid, tartaric acid, citric acid, lactic acid, maleic acid and methanesulphonic acid.

In the general formula I, $R_1$ preferably signifies a straight-chained $C_{10}$–$C_{14}$-alkyl group which can also be substituted by a $C_1$–$C_6$-alkoxy or a $C_1$–$C_6$-alkylmercapto group. In particular, $R_1$ represents a decyl, undecyl, dodecyl, tridecyl or tetradecyl group. As $C_1$–$C_6$-alkoxy substituents of $R_1$, the methoxy, ethoxy, butoxy and the hexyloxy groups. If $R_1$ is substituted by a $C_1$–$C_6$-alkylmercapto radical, one understands thereunder especially the methylmercapto, ethylmercapto, propylmercapto, butylmercapto or the hexylmercapto radical, and n is 0, 1 or 2.

$R_2$ preferably means a straight-chained $C_{10}$–$C_{14}$-alkyl group which can also be substituted by a $C_1$–$C_6$-alkoxy group or a $C_1$–$C_6$-alkylmercapto group. In particular, $R_2$ represents a decyl, undecyl, dodecyl, tridecyl or tetradecyl group. As $C_1$–$C_6$-alkoxy substituents of $R_2$, methoxy, ethoxy, propoxy, butoxy and the hexyloxy group.

If $R_2$ is substituted by a $C_1$–$C_6$-alkylmercapto radical, the methylmercapto, ethylmercapto, butylmercapto and hexylmercapto radical.

$R_4$ and $R_5$ each preferably signify hydrogen or one of the two radicals is preferably a cyano or azido group or a halogen atom, such as fluorine, chlorine, bromine or iodine.

Especially preferred are compounds in which $R_3$ and $R_4$ represent a hydrogen atom and $R_5$ is cyano, azido or fluorine, or $R_5$ is hydrogen, and $R_3/R_4$ represent a further bond between C-2' and C-3'.

In the bas B of the general formula I, the radicals $R_6$ and $R_7$ preferably signify a hydrogen atom, a methyl, ethyl, propyl or butyl radical or a halogen atom, such as fluorine, chlorine, bromine or iodine. Especially preferred for $R_6$ or $R_7$ is a hydrogen atom, the methyl or ethyl radical or a chlorine or bromine atom.

The radical $R_8$ is preferably a hydrogen atom, a methyl, ethyl, propyl or butyl radical, an amino group or a halogen atom, such as fluorine, chlorine, bromine or iodine, preferably chlorine or bromine.

$R_{10}$ preferably signifies a hydrogen, fluorine, chlorine or bromine atom, a $C_1$–$C_6$-alkoxy group, especially a methoxy, ethoxy, propoxy, butoxy or hexyloxy group, a $C_1$–$C_6$-alkylmercapto group, especially a methylmercapto, ethylmercapto, butylmercapto or hexylmercapto group, or an amino group, which can be mono- or disubstituted by a $C_1$–$C_6$-alkyl group, such as by the methyl, ethyl, butyl or hexyl group, by a hydroxy-$C_2$–$C_6$-alkyl group, such as the hydroxyethyl, hydroxypropyl, hydroxybutyl or hydroxyhexyl group, a $C_3$–$C_6$-cycloalkyl group, such as e.g. the cyclopropyl, cyclopentyl or cyclohexyl radical, aryl, preferably phenyl, an aralkyl radical, such as especially benzyl, which can possibly also be substituted by one or more hydroxyl or methoxy groups, by $C_1$–$C_6$-alkyl groups, such as the methyl, ethyl, propyl, butyl or hexyl group, or by halogen atoms, such as fluorine, chlorine or bromine. The amino group can also be substituted by a heterarylalkyl or hetaryl radical, such as the thienyl, the furyl or the pyridyl radical. By a heterarylalkyl radical, one preferably understands the thienylmethyl, furylmethyl or pyridylmethyl radical.

Preferred coupled nucleosides in the claimed liponucleotides of the general formula I are:
-2',3'-dideoxy-3'-azidouridine
-2',3'-dideoxyinosine
-2',3'-dideoxyguanosine
-2',3'-dideoxycytidine
-2',3'-dideoxyadenosine
-3'-deoxythymidine
-2',3'-dideoxy-2',3'-didehydro-$N^6$-(O-methylbenzyl)adenosine
-2',3'-dideoxy-2',3'-didehydro-$N^6$-(2-methylpropyl)adenosine
-2',3'-dideoxy-3'-azidoguanosine
-3'-deoxy-3'-azidothymidine
-2',3'-dideoxy-3'-3'-fluoro-5-chlorouridine
-3'-deoxy-3'-fluorothymidine
-2',3'-dideoxy-3'-fluoroadenosine
-2',3'-dideoxy-3'-fluoro-2,6-diaminopurineriboside
-2',3'-dideoxy-2',3'-didehydrocytidine
-3'-deoxy-2',3'-didehydrothymidine
-3'-deoxy-3'-azidothymidine.

The compounds of the general formula I can be prepared in that one 1. brings to reaction a compound of the general formula II,

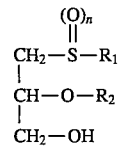

in which $R_1$, $R_2$ and n possess the given meanings, with a compound of the general formula III,

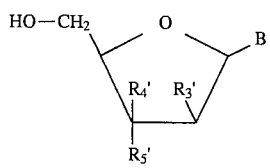

in which $R_3'$ represents hydrogen or a hydroxyl group protected by an oxygen protective group well known to the expert and $R_4'$ and $R_5'$ each represent hydrogen, halogen, an azido, a cyano or one of the radicals $R_4'$ and $R_5'$ signifies a hydroxyl group protected by an oxygen protective group well known to the expert or $R_3'$ and $R_4'$ represent a further bond and B possesses the meanings given supra, in the presence of phosphorus oxytrichloride and a phosphoric acid ester and a tert.nitrogen base, e.g. pyridine or triethylamine, in an inert solvent, such as e.g. toluene, and, after hydrolysis has taken place, possibly splits off the oxygen protective groups according to the processes usual in nucleoside chemistry, or 2. brings to reaction a compound of the general formula IV,

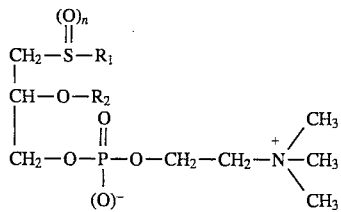

in which $R_1$, $R_2$ and n possess the above-given meanings, with a compound of the general formula III, in which $R_3'$, $R_4'$, $R_5'$ and B possess the given meanings, in the presence of phospholipase D in an inert solvent, such as e.g. chloroform, in the presence of a suitable buffer and, after reaction has taken place, possibly splits off the oxygen protective group corresponding to processes usual in nucleoside chemistry.

The preparation of the compounds of the general formula II and IV are described in Lipids 22, 947 (1987) and in DE-A-3039629.

The preparation of the compounds of the general formula III are described e.g. in EP-A 0 286 028 and WO 90/08147.

Compounds similar to the general formula I are described in EP-A-0350287. However, only 1,2-diesters of glycerol are there described.

The medicaments containing compounds of the formula I for the treatment of viral infections can be administered enterally or parenterally in liquid or solid form. The usual forms of administration, such as tablets, capsules, dragees, syrups, solutions or suspensions. As injection medium, water is preferably used which contains the additives usual for injection solutions, such as stabilizing agents, solubilizing agents and buffers. Such additives include tartrate and citrate buffers, ethanol, complex formers, such as ethylenediamine-tetraacetic acid and its non-toxic salts, and high molecular weight polymers, such as liquid polyethylene oxide, for viscosity regulation. Liquid carrier materials for injection solutions must be sterile and are preferably filled into ampuoles. Solid carrier materials are, for include, starch, lactose, mannitol, methyl cellulose, talc, highly dispersed silicic acids, high molecular weight fatty acids, such as stearic acid, gelatin, agar-agar, calcium phosphate, magnesium stearate, animal and vegetable fats, solid high molecular weight polymers, such as polyethylene glycol etc. Compositions suitable for oral administration can, if desired, contain flavouring and sweetening materials.

The dosage can depend upon various factors, such as mode of administration, species, age or the individual's state of health. The compounds according to the invention are usually administered in amounts of 0.1–100 mg, preferably of 0.2–80 mg per day per kg of body weight. It is preferred to divide up the daily dose into 2–5 administrations, whereby, in the case of each administration, 1–2 tablets with an active material content of 0.5–500 mg are administered. The tablets can also be retarded, whereby the number of applications per day can be reduced to 1–3. The active material content of the time released tablets can amount to 2–1000 mg. The active material can also be given by continuous infusion, whereby the amounts of 5–1000 mg per day normally suffice.

In the meaning of the present invention, apart from the compounds mentioned in the Examples and those by combination of all meanings mentioned in the claims for the substituents, the following compounds of the formula I also come into question:

1. (2',3'-dideoxy-3'-fluoro-5-chlorouridine)-5'-phosphoric acid (3-dodecylmercapto-2-decyloxy)-propyl ester
2. (3'-deoxy-3'-azidothymidine)-5'-phosphoric acid (3-dodecylsulphinyl- 2-decyloxy)-propyl ester
3. (3'-deoxy-3'-azidothymidine)-5'-phosphoric acid (3-dodecylsulphonyl- 2-decyloxy)-propyl ester
4. (2',3'-dideoxycytidine)-5'-phosphoric acid (3-dodecylmercapto- 2-decyloxy)-propyl ester
5. (2',3'-dideoxyinosine)-5'-phosphoric acid (3-dodecylmercapto- 2-decyloxy)-propyl ester
6. (2',3'-dideoxyguanosine)-5'-phosphoric acid (3-dodecylmercapto- 2-decyloxy)-propyl ester
7. (2',3'-dideoxyadenosine)-5'-phosphoric acid (3-dodecylmercapto- 2-decyloxy)-propyl ester
8. (3'-deoxythymidine)-5'-phosphoric acid (3-dodecylmercapto- 2-decyloxy)-propyl ester
9. (3'-deoxy-2',3'-didehydrothymidine)-5'-phosphoric acid (3-dodecylmercapto-2-decyloxy)-propyl ester
10. (3'-deoxy-3'-fluorothymidine)-5'-phosphoric acid (3-dodecylmercapto-2-decyloxy)-propyl ester
11. (2',3'-dideoxy-3'-azidoguanosine)-5'-phosphoric acid (3-dodecylmercapto-2-decyloxy)-propyl ester
12. (2',3'-dideoxy-3'-fluoro-2,6-diaminopurineriboside)-5'-phosphoric acid (3-dodecylmercapto-2 -decyloxy)-propyl ester
13. [2',3'-dideoxy-2',3'-didehydro-$N^6$-(2-methylpropyl)-adenosine]-5'-phosphoric acid (3-dodecylmercapto-2 -decyloxy)-propyl ester
14. [2',3'-dideoxy-2',3'-didehydro-$N^6$-(o-methylbenzyl)-adenosine]-5'-phosphoric acid (3-dodecylmercapto-2 -decyloxy)-propyl ester
15. (2',3'-dideoxy-2',3'-didehydrocytidine)-5'-phosphoric acid (3-decylmercapto-2-dodecyloxy)-propyl ester
16. (2',3'-dideoxy-3'-fluoroadenosine)-5'-phosphoric acid (3-undecylmercapto-2-dodecyloxy)-propyl ester
17. (2',3'-dideoxy-3'-azidouridine)-5'-phosphoric acid (3-decylsulphonyl-2-dodecyloxy)-propyl ester
18. (2',3'-dideoxycytidine)-5'-phosphoric acid (3-decylmercapto- 2-decyloxy)-propyl ester
19. (2',3'-dideoxyinosine)-5'-phosphoric acid (3-dodecylmercapto- 2-dodecyloxy)-propyl ester
20. (3'-deoxy-3'-azidothymidine)-5'-phosphoric acid (3-tetradecylmercapto-2-decyloxy)-propyl ester
21. (3'-deoxy-3'-azidothymidine)-5'-phosphoric acid (3-pentadecylmercapto-2-decyloxy)-propyl ester
22. (2',3'-dideoxyinosine)-5'-phosphoric acid (3 -tridecylmercapto-2-decyloxy)-propyl ester
23. (2',3'-dideoxyinosine)-5'-phosphoric acid (3 -dodecylmercapto-2-octyloxy)-propyl ester.

EXAMPLE 1a (3'-Deoxy-3'-azidothymidine)-5'-phosphoric acid (3-dodecylmercapto-2-decyloxy)-propyl ester To a solution of 1.25 g (3 mmol) 3-dodecylmercapto-2-decyloxy-1propanol and 1.2 ml (8.6 mmol) triethylamine in 40 ml abs. ether are added dropwise, under nitrogen, at 0° C. 0.42 ml (4.5 mmol) $POCl_3$ and after-stirred for 45 min. The solution is allowed to warm to room temperature, added dropwise thereto a solution of 800 mg (3 mmol) 3'-desoxy-3'-azidothymidine (AZT) in a mixture of 15 ml abs. ether and 20 ml abs. toluene and stirred for 6 h. under reflux (TLC control).

After cooling, 50 ml of water were added thereto, the mixture stirred vigorously for 2 hours, the organic phase thereafter separated off, dried over $Na_2SO_4$ and evaporated in a rotary evaporator. The residue was purified by preparative column chromatography on silica gel 60 with dichloromethane/methanol 9:1 as eluent.

Yield 540 mg (24% of theory).

M.p. 187° C. sinters, 220°–223° C. decomp. with brown coloration, $^{31}$P-NMR:=0.59 ppm.

EXAMPLE 1b (3'-Deoxy-3'-azidothymidine)-5'-phosphoric acid (3-dodecylmercapto-2-decyloxy)-propyl ester Analogously to the procedure in Chem. Pharm. Bull. 36, 5020 (1988), 2 mmol AZT and 5000 U phospholipase D were suspended in 4 ml sodium acetate buffer/$CaCl_2$, mixed with a solution of 6 mmol 3-dodecylmercapto-2-decyloxypropyl-1-phosphoric acid monocholine ester in 160 ml chloroform and heated for 8 h. at 45° C. It was then dried over $Na_2SO_4$ and the solvent removed in a vacuum. The residue was purified by column chromatography as in Example 1. Yield 51%. The produce proved to be identical with the product of Example 1a (m.p., TLC, $^1$H- and $^{31}$P-NMR).

EXAMPLE 2

(3'-Deoxy-3'-azidothymidine)-5'-phosphoric acid (3-undecylmercapto-2-undecyloxy)-propyl ester was prepared analogously to Example 1a. Yield 27%, m.p. 218°–222° C. (decomp.).

EXAMPLE 3

[2',3'-Dideoxy-2',3'-didehydro-$N^6$-(o-methylbenzyl)adenosine-5'-phosphoric acid (3-dodecylmercapto-2-decyloxy)-propyl ester 680 mg (1.37 mmol) phosphoric acid (3-dodecylmercapto-2-decyloxy)-propyl ester in 20 ml abs. pyridine were mixed with 337 mg (1 mmol) 2',3'-dideoxy- 2',3'-didehydro-$N^6$-(O-methylbenzyl)-adenosine and, after addition of 1.37 g (6.7 mmol) DCC, stirred for 24 hours at room temperature (TLC control). The pyridine was then removed in a vacuum, the residue suspended in ether and filtered off from the undissolved urea. The filtrate was purified, after the evaporation of the solvent, by column chromatography on silica gel 60 with dichloromethane/methanol 95/5 as eluent. Yield 220 mg (26% of theory). $R_f$=0.68 ($CH_2Cl_2$/$CH_3OH$/$H_2O$ 13/5/0.8).

EXAMPLE 4

(3'-Deoxy-3'-azidothymidine)-5'-phosphoric acid (3-dodecylmercapto-2-decyloxy)-propyl ester Analogously to Example 3, from 13.5 g phosphoric acid (3-dodecylmercapto-2-decyloxy)-propyl ester, 5.4 g AZT and 27 g DCC in 350 ml abs. pyridine, by 30 hours stirring at room temperature and purification as described above, there is prepared the corresponding liponucleotide in 62% yield (analytical data identical with those of Example 1).

EXAMPLE 5

(3'-Deoxythymidine)-5'-phosphoric acid (3-dodecylmercapto- 2-decyloxy)-propyl ester Analogously to Example 3, from 1.3 g phosphoric acid (3-dodecylmercapto-2-decyloxy)-propyl ester, 500 mg 3'-desoxythymidine and 2.6 g DCC in 40 ml abs. pyridine, by 24 hours stirring at room temperature and chromatographic purification, the corresponding liponucleotide was obtained in 51% yield. $R_f$=0.45 ($CH_2Cl_2$/$CH_3OH$/$H_2O$ 12/5/0.8).

EXAMPLE 6

(2',3'-Dideoxyinosine)-5'-phosphoric acid (3-dodecylmercapto- 2-decyloxy)-propyl ester Analogously to Example 3, from 1.3 g phosphoric acid (3-dodecylmercapto-2-decyloxy)-propyl ester, 500 mg 2',3'-didesoxyinosine and 2.6 g DCC in 40 ml abs. pyridine, by 40 hours stirring at room temperature and chromatographic purification, the said liponucleotide was prepared in 61% yield. $R_f$=0.38 ($CH_2Cl_2$/$CH_3OH$/$H_2O$ 13/5/0.8).

We claim:

1. The compound (3'-deoxy-3'-azidothymidine)-5'-phosphoric acid (3-undecylmercapto-2-undecyloxy)-propyl ester.

2. The compound (3'-deoxy-3'-azidothymidine)-5'-phosphoric acid (3-decylthio-2-decyloxy)-propyl ester.

3. The compound (3'-deoxy-3'-azidothymidine)-5'-phosphoric acid (3-dodecylsulphinyl-2-decyloxy)-propyl ester.

4. The compound (3'-deoxy-3'-azidothymidine)-5'-phosphoric acid (3-dodecylsulphonyl-2-decyloxy)-propyl ester.

5. The compound (3'-deoxy-3'-azidothymidine)-5'-phosphoric acid (3-dodecylmercapto-2-decyloxy)-propyl ester.

6. The compound (3'-deoxy-3'-fluorothymidine)-5'-phosphoric acid (3-dodecylmercapto-2-decyloxy)-propyl ester.

7. A physiologically acceptable salt of the compound of claim 1.

8. A physiologically acceptable salt of the compound of claim 2.

9. A physiologically acceptable salt of the compound of claim 3.

10. A physiologically acceptable salt of the compound of claim 4.

11. A physiologically acceptable salt of the compound of claim 5.

12. A physiologically acceptable salt of the compound of claim 6.

13. Pharmaceutical composition comprising the compound of claim 1 or a physiologically acceptable salt thereof and a pharmaceutically acceptable carrier.

14. Pharmaceutical composition comprising the compound of claim 2 or a physiologically acceptable salt thereof and a pharmaceutically acceptable carrier.

15. Pharmaceutical composition comprising the compound of claim 3 or a physiologically acceptable salt thereof and a pharmaceutically acceptable carrier.

16. Pharmaceutical composition comprising the compound of claim 4 or a physiologically acceptable salt thereof and a pharmaceutically acceptable carrier.

17. Pharmaceutical composition comprising the compound of claim 5 or a physiologically acceptable salt thereof and a pharmaceutically acceptable carrier.

18. Pharmaceutical composition comprising the compound of claim 6 or a physiologically acceptable salt thereof and a pharmaceutically acceptable carrier.

* * * * *